United States Patent [19]
Greco

[11] Patent Number: 5,219,979
[45] Date of Patent: Jun. 15, 1993

[54] POLYOXAZOLIDINES WITH A STRUCTURE CONTAINING CARBONATE GROUPS, PROCEDURE FOR THEIR PREPARATION AND USE

[75] Inventor: Alberto Greco, Milan, Italy

[73] Assignee: Enichem Synthesis S.p.A., Palermo, Italy

[21] Appl. No.: 833,112

[22] Filed: Feb. 10, 1992

[30] Foreign Application Priority Data

Feb. 11, 1991 [IT] Italy .............................. 000345 A/91

[51] Int. Cl.$^5$ .......................................... C08G 14/073
[52] U.S. Cl. .................................... 528/220; 528/229; 528/230; 528/266; 528/269; 528/405; 528/406; 528/423; 525/398; 525/399; 525/452; 525/471; 525/509; 525/540; 525/909
[58] Field of Search ............... 528/220, 229, 230, 266, 528/269, 405, 406, 423; 525/398, 399, 452, 471, 509, 540, 909

[56] References Cited

U.S. PATENT DOCUMENTS

| 3,743,626 | 7/1973 | Emmons | 428/355 |
| 3,864,335 | 2/1975 | Emmons | 548/215 |
| 4,138,545 | 2/1979 | Emmons et al. | 528/289 |
| 4,296,225 | 10/1981 | Rhum | 526/260 |

FOREIGN PATENT DOCUMENTS

| 0087659 | 9/1983 | European Pat. Off. |
| 0228935 | 7/1987 | European Pat. Off. |
| 0387926 | 9/1990 | European Pat. Off. |
| 2359161 | 2/1978 | France |

*Primary Examiner*—John Kight, III
*Assistant Examiner*—Sam A. Acquah
*Attorney, Agent, or Firm*—Oblon, Spivak, McClelland, Maier & Neustadt

[57] ABSTRACT

New polyoxazolidines can be defined with the general formula:

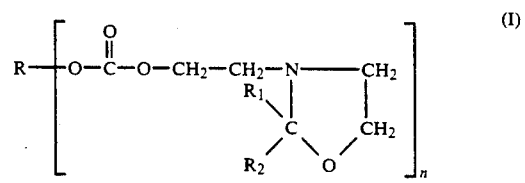

(I)

where R, $R_1$, $R_2$ and n have the meaning specified in the description. These polyoxazolidines are useful cross-linking agents for hydrocuring systems based on polyisocyanates, acrylate polymers and polyepoxides, in compositions for paints, coatings, sealants and adhesives.

3 Claims, 1 Drawing Sheet

POLYOXAZOLIDINES WITH A STRUCTURE CONTAINING CARBONATE GROUPS, PROCEDURE FOR THEIR PREPARATION AND USE

BACKGROUND OF THE INVENTION

1. Field of the Invention

The present invention relates to new polyoxazolidines, the procedure for their preparation and their use as cross-linking agents for hydrocuring systems based on polyisocyanates, acrylate polymers and polyepoxides in compositions for paints, coatings, sealants and adhesives.

2. Discussion of the Background

U.S. Pat. No. 3,743,626 describes the use of some polyoxazolidines as curing agents in conditions of normal temperature and moisture, for adhesives based on both aromatic and aliphatic polyisocyanates. As described in U.S. Pat. No. 4,138,545, these polyoxazolidines can be obtained by means of a reaction of an oxazolidine (A):

with lower alkyl ethers of dicarboxylic or polycarboxylic acids, by transesterification or by means of a reaction of an oxazolidine (B):

with a glycol or polyol, under transesterification conditions. The oxazolidines (B) are in turn obtained by adding aldehydes to an addition product between ethanol amine and an alkyl acrylate.

These transesterification reactions are generally carried out in the presence of catalysts and the polyoxazolidines thus obtained have ester groups which can easily undergo hydrolysis.

Belgian patent 856.893 describes the use of some polyoxazolidines in sealant compositions based on polyisocyanates. As described in Belgian patent 833.821, these polyoxazolidines can be obtained by the addition of the oxazolidine (A) to polyisocyanates. These products have the disadvantage of cost and toxicity due to the polyisocyanates. In addition, owing to the formation of urethanes in their synthesis, the viscosity of these products is too high, especially when non-aliphatic diisocyanates or polyisocyanates in general are used.

European Patent Application No.228.935 describes the use of polyoxazolidines as cross-linking agents in sealing compounds based on polyisocyanates, cross-linkable in normal conditions of moisture. These polyoxazolidines use bisalkanolamines (C) as starting products:

The synthesis of these alkanolamines, starting from amines and ethylene oxide, is not very selective. It is also necessary to separate these reaction products from the reaction mass, under conditions of high temperature and vacuum. Distillation is necessary to eliminate the tertiary amines (tri- and poly-alkanolamines) which, if introduced into the polyisocyanate systems, reduce their life due to early cross-linking, both chemically (alkanols) and catalytically (presence of tertiary nitrogen).

U.S. Pat. No. 4,296,225 describes the use of polyoxazolidines as latent cross-linking systems, in polyvinylic systems, in the preparation of polyvinylic emulsions. In this case, the oxazolidine is used in the form of hydroxyalkyloxazolidine methacrylate, or as a component in polyurethane paints having a high solid content. The principle consists of inserting the oxazolidinic nucleus into a polyacrylate, which is made possible by using a vinyloxazolidine capable of copolymerizing to various degrees with the acrylic monomers. In any case, the oxazolidinic equivalent is not high and the polymers are excessively viscous solids or liquids, making it necessary to disperse them in water or dissolve them in an organic solvent.

These drawbacks of the known art have been brilliantly overcome by the Applicant in Italian Patent Application No. 19089A/89 which describes a group of polyoxazolidines which can be prepared both easily and practically and which can be used as cross-linking agents in hydrocuring systems based on polyisocyanates, acrylate polymers or polyepoxides.

The only disadvantage of this product is the presence of one or more thioether bridges in the structural formula, which although giving stability to photo-oxidation and better oleo-resistance to the manufactures into which these products have been incorporated, generally have an unpleasant odour, typical of polysulphides.

SUMMARY OF THE INVENTION

The present invention relates to a new group of polyoxazolidines which overcomes the disadvantages of the known art mentioned above. In particular, a new group of polyoxazolidines has been found, in accordance with the present invention, which can be prepared both easily and practically and which can be used as cross-linking agents in hydrocuring systems based on polyisocyanates, acrylate polymers or polyepoxides, when high fluidity in the liquid state at normal temperature is required, together with a good chemical, thermal and aging resistance in fields of application such as paints, sealants and adhesives and an excellent resistance to hydrolysis in the end products.

DETAILED DESCRIPTION OF THE PREFERRED EMBODIMENTS

In accordance with this, a first aspect of the present invention relates to new polyoxazolidines corresponding to the general formula:

(I)

where, n is a number between 1 and 10, R is an n-valent radical selected from:
A N-ethyl-oxazolidinic radical, the trivalent triethylisocyanurate radical, an alkylenic n-valent radical with a linear or branched chain, containing from 2 to 12 carbon atoms or a cycloalkylenic radical containing from 5 to 12 carbon atoms, the alkylic residue of a polyethyleneglycol —(CH$_2$—CH$_2$—O)$_m$—CH$_2$—CH$_2$—, m being a number between 1 and 4, the para-dimethyl-encyclohexane biradical, or R is a n-valent radical having the general formula:

where R$_3$ is the linear, cyclic or arylic hydrocarbon residue of a glycol containing up to 12 carbon atoms, whereas R$_4$ has the same meaning as R excluding R=N-ethyl-oxazolidinic radical; R$_1$ and R$_2$, the same or different, represent the hydrogen atom, an alkyl radical, with a linear or branched chain, containing from 1 to 6 carbon atoms, a cycloalkyl radical or an aryl radical or, R$_1$ and R$_2$, together with the carbon atom between them, represent a saturated cycloalkylic ring with 5, 6, or 7 carbon atoms.

For the purposes of the present invention, the term "Aryl" refers to a mono- bi-, or tri-cyclic aromatic radical containing from 6 to 14 carbon atoms, possibly substituted.

In the preferred form, R represents a linear or branched bi- tri- or tetra-valent alkylenic radical containing from 2 to 6 carbon atoms or a cycloalkylenic radical; R$_1$ and R$_2$ represent independently an alkyl radical, with a linear or branched chain, containing from 1 to 4 carbon atoms, or either R$_1$ or R$_2$ represents the hydrogen atom and the other represents an alkyl radical, with a linear or branched chain, containing from 1 to 4 carbon atoms.

Typical examples of bivalent alkylenic or cycloalkylenic radicals are:

Typical examples of a trivalent alkylenic radical are:

whereas a typical example of a tetravalent alkylenic radical is composed of the radical:

The polyoxazolidines in accordance with the present invention can be obtained as illustrated in the following diagram of reactions, where, in the formulae, R, R$_1$, R$_2$, and n have the meaning specified above.

oxygen atoms and the carbon atom between them, form a cyclic carbonate with 5 or 6 atoms of the kind where m is a number between 2 and 3.
Preferred carbonates are:

More specifically, with reference to the above diagram, the dihydroxyethylenediamine (III) is reacted with an aldehyde or a ketone (II) (depending on whether $R_1$ or $R_2$ represent the hydrogen atom or an alkyl radical to give N-hydroxyethyl-oxazolidine (IV). Examples of aldehydes and ketones which can be used for the purpose are formaldehyde, isobutyric aldehyde, acetone, methylethylketone, cyclopentanone and cyclohexanone. It is preferable to use isobutyric aldehyde or methyl ethyl ketone. The reaction between (II) and (III), which is known in the art together with the hydroxyethyloxazolidine (IV) obtained from it, is preferably carried out at a temperature ranging from 20° to 160° C., without solvent, by refluxing the aldehyde or ketone so as to azeotropically eliminate the water which is formed as a subproduct of the reaction. In this case, the aldehyde or ketone is used in an excess of 20-100% of the stoichiometric amount, or in the presence of a chemical dehydrator.

Alternatively, an aliphatic or aromatic solvent can be used, which is capable of forming an azeotropic mixture with water. In this case, a slight excess of the aldehyde or ketone on the stoichiometric amount is used, generally of between 5 and 20%. The reaction is moderately exothermic and lasts for a period of from 4-10 hours, depending on the temperature. At the end of the reaction, the solvent, if any, and excess aldehyde or ketone are eliminated.

The hydroxyethyloxazolidines can be used as such or preferably and only when this is possible, they can be purified by distillation under a reduced vacuum of 0.1-1 mm. Hg at temperatures ranging from 50° to 150° C. depending on the nature of $R_1$ and $R_2$.

To facilitate the reaction, a small quantity of an acid catalyst can be added to encourage condensation, such as paratoluenesolfonic acid, solfonate resins etc. Operating under the above conditions practically quantitative yields of the product are obtained.

The subsequent transesterification reaction is carried out in the presence of hydroxyethyloxazolidine (IV), a polyol (VI), where R has the meaning specified above, and a carbonate (V), where $R_5$ and $R_6$ represent a saturated or unsaturated hydrocarbon radical containing from 1 to 4 carbon atoms or an aryl radical, or $R_5$ and $R_6$, taken contemporaneously with the two adjacent Among the polyvalent alcohols (VI) $R(OM)_n$, it is preferable to use di-, tri- and tetra-ethyleneglycol, 1,4-dihydroxymethylcyclohexane, 1,4-butandiol, 2,2-diethyl-butan-1,4-diol, 2,2 dimethyl-1,3-propandiol, glycerine, trimethylol propane, trihydroxyethylisocyanurate, pentaerythritol.

The transesterification reaction is generally carried out at temperatures ranging from 60° to 160° and preferably between 100° C. and 140° C. in the presence of a transesterification catalyst. The preselected temperatures are sufficient to remove alcohols $R_5OH$ and $R_6OH$ (or the glycol or phenols depending on the nature of radicals $R_5$ and $R_6$) which are distilled off as soon as they are formed.

The transesterification process is in this case carried out at atmospheric pressure. Alternatively, it is possible to operate at a partially reduced pressure to facilitate the removal of the alcohols $R_5OH$ and $R_6OH$.

The transesterification reaction does not require strict stoichiometric amounts.

It is preferably carried out with an excess of hydroxy ethyloxazolidine (IV), which can reach 30% of the stoichiometric quantity.

In this case, when the transesterification reaction has been completed, the excess hydroxyethyloxazolidine (III) is removed by distillation, possibly under reduced pressure.

If the transesterification reaction is carried out with a not very volatile oxazolidine (when $R_1$ and $R_2$ represent particularly heavy groups), it is preferable to operate with an excess of carbonate (V) instead of with an excess of hydroxyethyloxazolidine whose unreacted part is difficult to remove at the end of the reaction; even in this case, the unreacted carbonate is removed by distillation under reduced pressure at the end of the reaction. When the reaction is complete and after the removal of any possible residual quantities of hydroxyethyloxazolidine or carbonate by distillation, the product obtained is cooled and the catalyst eliminated, using the most suitable techniques for the catalytic system used.

Transesterification catalysts which can be used are: either an alkaline metal, a sodium or potassium alcoholate of a low-boiling alcohol, or an organometallic compound of $Sn_{IV}$, $Ti_{IV}$ or other metals; preferably sodium methylate is used.

The quantity of catalyst used varies from 50 to 1000 ppm with respect to the mixture of reactants.

If sodium methylate is used as catalyst, its removal at the end of the reaction involves neutralization with an organic or inorganic acid used in a stoichiometric quantity or preferably in slight excess (50-30%) with respect to the sodium methylate. Any free acidity is removed by treatment with calcium oxide and subsequent filtration.

The polyoxazolidine (I) is obtained with almost quantitative yields.

The advantage of polyoxazolidinic structures of the carbonate type corresponding to formulae (I) compared to those of the polyester type of the known art is that the end products have a higher hydrolytic resistance as shown in the enclosed examples.

The procedure for the preparation of the polyoxazolidines (I) in accordance with the present invention has various advantages. The main advantage is that there is a high yield and selectivity of the reactions involved. In addition, stable and easily manageable intermediates are used together with catalysts which are not harmful for the polyisocyanates, making it possible to incorporate the polyoxazolidines of the present invention into the systems of isocyanates without prejudicing the pot stability. Finally, the procedure is flexible in that it gives a variety of polyoxazolidines with a wide degree of functionality, generally ranging from 2 to 10.

The polyoxazolidines (I) of the present invention are compatible with the most common groups of organic polymers.

The polyoxazolidines (I) of the present invention form latent catalysts in that they hydrolyze instantly in the presence of humidity, even natural humidity, with an opening of the oxazolinic ring and the generation of polyalkanol amines. They are consequently useful as cross-linking agents of polyisocyanates, polyepoxides and polyacrylates (Michael addition) in compositions of paints, sealants and adhesives. These polyoxazolidines are particularly useful combined with polyisocyanates, in that, owing to their intrinsic characteristics, they do not prejudice their life and can consequently be combined with these in monocomponent systems, which are fluid in normal conditions, with solvents and cross-linkable at ambient humidity. In these formulations the low viscosity of the polyoxazolidines is particularly favourable.

Suitable polyisocyanates for these formulations are both the trimers of hexamethylenediisocyanate and isophorone isocyanate and the trimers obtained by the partial addition of water to diisocyanates in general and to those obtained starting from aliphatic and/or aromatic diisocyanates and polyols or organic, difunctional and polyfunctional polymers, with a low molecular weight (around 500-20,000), and with hydroxylic functionality at the chain end. Among these, reference may be made to polyesters, polyethers, polycarbonates, polybutadienes and some hybrid polymers such as polycarbonates copolyethers and polycarbonates copolyesters, with a hyroxylic chain-end.

These polyisocyanates are used in composition together with the polyoxazolidines of the present invention in such a way that two equivalents of isocyanate groups in the polyisocyanate correspond to every oxazolidinic equivalent in the polyoxazolidine. Variations in this stoichiometry are possible, without excessively prejudicing the solidity of the cross-linked products, provided that the polyoxazolidine is preferably present in quantities from 30% in defect to 10% in excess with respect to the stoichiometric value.

The formulation between polyisocyanates and polyoxazolidines can be carried out within a temperature range of normal values to 60° C., and is facilitated by the perfect compatibility of the two products involved. Catalysts suitable for accelerating the cross-linking, may be present in the formulation, normally selected from metallic soaps, and in particular organometallic compounds of tin, and from organic acids, and in particular p-toluenesulphonic acid, naphatoic acid etc. Besides catalysts, other additives may be incorporated such as organic or inorganic charges, thixotropic agents, flame-resistant agents, adhesion promoters, stabilizers, UV absorbers, in accordance with the method used.

The formulations thus obtained cross-link at a high rate, owing to the atmospheric humidity, in end-products having excellent characteristics, especially with respect to thermal and chemical resistance and resistance to photo-oxidative aging.

The following experimental examples provide a further illustration of the invention.

EXAMPLE 1

Preparation of 2 hydroxy-N-ethenyl-(2-isopropyl)-1,3 oxazolidine (g 580.65; 3.6519 moles); diallylcarbonate (DAC) (g 235.9; 1.6599 moles) and sodium methylate in $CH_3OH$ (3 ml of a 30% solution by weight) are charged, under a nitrogen flow, into a flask equipped with a magnetic bar stirrer and a distillation tower with 5 theoretical plates and nitrogen inlet.

The transesterification was carried out at +120° C. progressively reducing the vacuum to 30 torr for the duration of 4 hours, at the end of which allylalcohol was distilled (g 180, 3.108 moles; 84% of the theoretical value).

The vacuum was brought to 0.5 torr and the excess hydroxyethyloxazolidine was eliminated, the temperature of the distillation tower being brought from +25° to +100° C. The hydroxyethyloxazolidine was thus recovered in 3 hours. The temperature at which the hydroxyethyloxazolidine passes is of +76° C. at the head of the column (g 878, 0.49 moles).

The heated product was cooled, treated with p-toluene sulphonic acid (g 3.8; moles 0.195) in methylethylketone (10 cc) for 30' at room temperature and finally with calcium oxide (15 g) for 60'.

After filtration, the product gave the following analysis: C=57.35, H=9.90; N=7.98 (the product requires a structure of $C_{17}H_{32}O_5H_2$, and a PM=344; C=58.3; H=9.3; N=8.14).

The product has a viscosity of 35-40 cps (+25° C.), is transparent and orange in colour, sulphur and free acidity absent.

Figure 1:
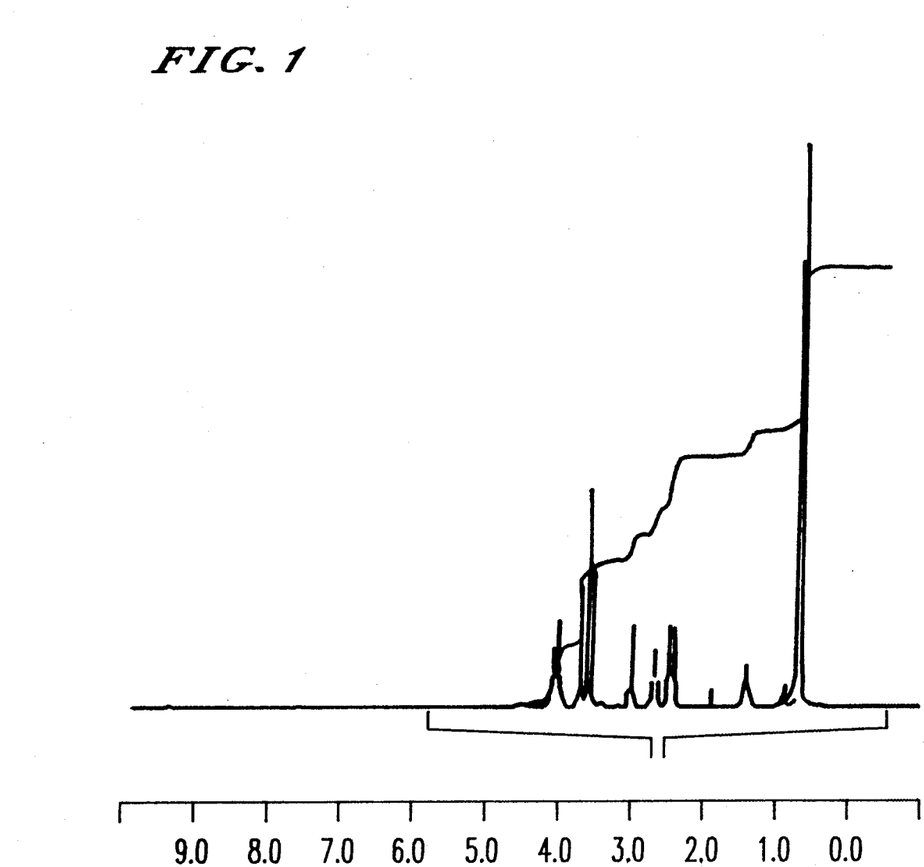
FIG. 1 shows the NMR spectrum of the product produced by Example 1.

The yield was g 550, 1,599 moles, 96.3% yield on DAC. The structural formula was confirmed by NMR (see FIG. 1 enclosed).

The IR spectrum carried out on the product showed a peak at cm⁻¹ 1740 coresponding to the carbonate bridge and no peak due to residual allylic groups (cm⁻¹ 1665).

EXAMPLE 2

Preparation of:

$$\begin{array}{c}
CH_2-O-\overset{O}{\underset{\|}{C}}-O-CH_2-CH_2-N\overset{CH_2}{\underset{H_3C}{\diagdown}}\overset{}{\underset{CH-CH}{\diagup}}\overset{CH_2}{\underset{O}{\diagdown}} \\
\bigcirc H \\
CH_2-O-\underset{\|}{C}-O-CH_2-CH_2-N\overset{CH_2}{\underset{H_3C}{\diagdown}}\overset{}{\underset{CH-CH}{\diagup}}\overset{CH_2}{\underset{O}{\diagdown}} \\
O \\
H_3C
\end{array}$$

The same procedure as Example 1 is used, starting with hydroxyethyloxazolidine (g 349.8, 2.2 moles), cyclohexane dimethanol (g 144.2, 1.0 moles), diallyl carbonate (g 284.24, 2.0 moles) and sodium methylate (ml 2, 30% solution in methanol).

The light distillate composed of allyl alcohol (95%) amounts to g 242.1 (moles 3.98, 99% of the theoretical value).

The hydroxyethyloxazolidine recovered amounts to g 58.5 (0.36 moles).

The yield of the product generally represented by the above structure is 472.8 g (moles 0.918, 91.8% yield).

The elemental analysis gives C=60.36, H=9.14, N=5.1 (a $C_{26}H_{46}O_8N_2$ structure, having PM 514 requires C=60.7, H=8.95, N=5.45).

The product is treated with p-toluenesulphonic acid for neutralization and finally with CaO, exactly as specified in Example 1. Filtration on Celite at +70° C. eliminates any free acidity (Sulphur 1 ppm). The product tends to become opalescent.

The IR spectrum of the product showed a single peak at cm⁻¹ 1745 corresponding to the structure $$-O-\underset{\|}{\overset{O}{C}}-O-;$$

the NMR analysis of the product confirmed the proposed structure.

EXAMPLE 3

Preparation of:

$$CH_3-CH_2-C\begin{pmatrix}CH_2-\\CH_2-\\CH_2-\end{pmatrix}\left[O-\underset{\|}{\overset{O}{C}}-O-CH_2-CH_2-N\overset{CH_2}{\underset{H_3C}{\diagdown}}\overset{}{\underset{CH-CH}{\diagup}}\overset{CH_2}{\underset{O}{\diagdown}}\right]_3$$

Using the same equipment and procedure as described in Example 1, trimethylolpropane (TMP) (g 134.5; moles 1), hydroxyethyloxazolidine (g 524.7, moles 3.3) and diallyl carbonate are charged into the flask.

The transesterification is carried out under the same conditions of temperature and pressure as specified in Example 1 and in the presence of sodium methylate (ml 2 of a 30% solution by weight in methanol). The subsequent treatment to eliminate the excess, unreacted oxazolidine is the same as that described in Example 1.

680 g (0.987 moles) of the end product are obtained (98.7% yield).

Elemental analysis gives C=56.95, H=9.48, N=6.1 (the product having formula $C_{33}H_{59}H_3O_{12}$ requires PM=689, C=57.47, H=8.56, N=6.1).

The product is in the form of a homogeneous liquid with a viscosity of 2720 cps at +25° C.

The catalyst is eliminated using the usual method with p-toluenesulphonic acid and then CaO and subsequent filtration at +100° C. on Celite.

The IR spectrum showed the usual peak at 1746 cm⁻¹ and NMR analysis confirmed the proposed structure.

EXAMPLE 4

Preparation of $$\begin{bmatrix}\overset{N}{\underset{O=C\diagup \diagdown C=O}{}}\overset{CH_2-CH_2-}{\underset{-N\diagdown \diagup N-CH_2-CH_2-}{}}\overset{}{\underset{C}{\|}}\overset{}{\underset{O}{}}\overset{}{\underset{-CH_2-CH_2-}{}}\end{bmatrix}\left[O\underset{\|}{\overset{}{C}}-O-CH_2-CH_2-N\overset{CH_2}{\underset{H_3C}{\diagdown}}\overset{}{\underset{CH-HC}{\diagup}}\overset{CH_2}{\underset{O}{\diagdown}}\right]_3$$

Operating under the same conditions and with the same procedure as in Example 1, the transesteriication is carried out with trihydroxyethylisocyanurate (g 265; 1 mole), hydroxy ethyloxazolidine (g 511, 3.025 moles), diallylcarbonate (g 433, 3.041 moles) in the presence of sodium methylate (30% in CH₃OH, ml. 3). At the end of the reaction (8 hours) 362 g of light distillate composed of 15 g of dihydroxyethyloxazolidine were obtained, whereas the required reaction product remains in the flask and is treated first with p-toluenesulphuric acid (3.6 g in 10 ml of methylethylketone), then with CaO (15 g) and is finally filtered.

This amounts to 738 g (97.8% of the theoretical value) and is in the form of a limpid, transparent liquid whose elemental analysis gave the following results: C=52.4, H=7.68, N=9.93, (a product having formula $C_{36}H_{60}N_6O_{15}$ requires PM 816, C=52.94, H=7.35, N=10.29).

The NMR analysis confirmed the proposed structure, whereas the IR spectrum showed two carbonylic peaks at 1700 and 1750 cm$^{-1}$ respectively due to the CO in the isocyanuric ring and to the carbonate bridge.

EXAMPLE 5

Preparation of the same product as Example 1 starting from dimethylcarbonate instead of diallylcarbonate.

Hydroxyethyloxazolidine (g 1408, moles 8.85), dimethylcarbonate (g 1185, moles 13.16) and sodium methylate (30% alcohol solution by weight, 6 ml, 0.0333 moles) are charged into the same reactor as Example 1.

Transesterification is carried out at an internal temperature of +115° C. at atmospheric pressure, then under reduced vacuum and finally maximum vacuum (0.1 torr) for a total period of 10 hours.

During the distillation phase at atmospheric pressure, 306 g and in the reduced vacuum phase 814 g of distillate are recovered, giving a total amount of 1120 g. When subjected to gas chromatography, this product is proved to consist of methanol (g 278, 97.8% of the theoretical value) and DMC (788 g, 100% of the theoretical value). The heated product amounts to g 1467 (4.26 moles; 96.4% yield).

The heated product brought to room temperature was neutralized by slowly adding dropwise and under stirring monohydrate p-toluenesulphonic acid (g 6.28, moles 0.033) dissolved in MEK (50 ml). After stirring for 1 hour CaO was added in powder form (g 20), together with anhydrous MgSO$_4$ (g 20) and freshly distilled isobutyraldehyde (ml 29, g 22.5). After stirring for 4 hours at room temperature, the product was filtered on a Celite bed; the yield was 1529 g, 95.9% of which was represented by the above product which had the following characteristics:

| | |
|---|---|
| colour: | pale yellow |
| aspect: | limpid, transparent |
| density: | (+20° C.) 1.04 |
| viscosity: | (Cps, +25° C.) 33 | and the following elemental analysis: C=58.52, H=9.59, N=7.37; S absent, calculated purity 95%.

EXAMPLE 6

Application of the polyoxazolidines obtained in Examples 1-5 in the formulation of sealants.

Prepolymers having NCO end groups were used in two different types of plasticizer, i.e. respectively commercial products MESAMOL (phenolalkylsulphonate) and benzyl butyl phthalate (see in Table 1 % weight of plasticizer of the total composition).

The prepolymers having —NCO end groups were obtained by reacting the commercial product Ravecarb 107 (of Enichem Synthesis) which is a liquid polycarbonate with a hydroxy end-qroup and having formula:

wherein the two repeat units are obviously distributed at random, n and m are two such numbers that the MW of the product is 1850 whereas the number of OH is 64 expressed as mg of KOH/g of polycarbonate, or a copolyester polycarbonate (commercial product RAVE-CARB 111 of Enimont Synthesis) with MN 2000, No. of OH=56 (expressed as above) or a commercial polycarbonatediol of hexanediol (RAVECARB 102 of Enichem Synthesis) having a number average molecular weight Mn=1000 and number of OH=112 expressed as above with isophorondiisocyanate in a ratio -NCO/-OH=2.05.

The prepolymers diluted in the plasticizer as specified above were formulated with the polyoxazolidines produced in Examples 1-5 in the proportions indicated in Table 1 and with 350 ppm of tin dibutyldilurate, in the form of 2 mm thick sheets.

TABLE 1

| Test No | Polyoxazolidine Example No | g | meq (OH + NH) | Prepolymer in plasticizer g | meq NCO | RAVECARB Type x% relative weight | Plasticizer type | weight % |
|---|---|---|---|---|---|---|---|---|
| 1 | 3 | 7.4 | 64.4 | 100 | 61.2 | RAV 107 + 111 35% + 65% | Mesamoll | 27 |
| 2 | 1 | 13.4 | 155.8 | 144.8 | 155.8 | RAV 102 | Benzyl butyl phthalate | 30 |
| 3 | 4 | 15.7 | 115.4 | 194 | 120 | RAV 107 + 111 35% + 65% | Mesamoll | 27 |
| 4 | 1 | 5.58 | 64.8 | 100 | 61.2 | RAV 107 + 111 35% + 65% | Mesamoll | 30 |
| 5 | 2 | 9.4 | 73.16 | 116.3 | 76.7 | RAV 111 | Benzyl butyl phthalate | 20 |
| 6 | 2 | 9.0 | 70.0 | 115.4 | 73.2 | RAV 107 + 111 40% + 60% | Mesamoll | 30 |

*RAV = Ravecarb and relative percentages by weight if mixed with each other
**the percentages by weight of RAV + isoforonysocyanate in each test are complements to 100 of the amount of plasticizer shown in the last column of Tab. 1

An examination of the sheets previously obtained, after 30 days of cross-linking at normal humidity and temperature, gave the results shown in Table 2.

TABLE 2

| Test No. | Gel % (1) | Shore hardness A | Thickness (mm) | U T S (2) (N/mm$^2$) | Modulus (3) 100% | Elongat. to brake (%) |
|---|---|---|---|---|---|---|
| 1 | 67 | 55 | 1.50 | 2.85 | 1.56 | 225 |
| 2 | nd | 63 | 2.02 | 3.43 | 2.36 | 166 |

TABLE 2-continued

| Test No. | Gel % (1) | Shore hardness A | Thickness (mm) | U T S (2) (N/mm$^2$) | Modulus (3) 100% | Elongat. to brake (%) |
|---|---|---|---|---|---|---|
| 3 | 66 | 54 | 1.63 | 2.68 | 1.29 | 287 |
| 4 | 67 | 50 | 1.25 | 2.52 | 1.31 | 282 |
| 5 | nd | — | 1.67 | 2.5 | 1.02 | 297 |
| 6 | 67.5 | 48 | 1.79 | 2.94 | 0.92 | 409 |

(1) determined by exhaustive extraction with methylene chloride at room temperature
(2) U T S = ultimate tensile strength: ASTM
(3) modulus at 100% elongation expressed as N/mm$^2$

EXAMPLE 7

The same polyoxazolidines prepared as described in Examples 1-5 were used in the formulation of paints with the addition of the commercial product Desmodur N75 of Bayer (75% by weight in xylene of the trimer of hexamethylene diisocyanate).

The relative quantities of the two products are expressed in milliequivalents —(1 equivalent of polyoxazolidine corresponds to M/2n where M is the average molecular weight of the polyoxazolidine whereas n has the meaning defined in the text; for example n=2 for the polyoxazolidines of Examples 1 and 2 whereas n=3 in the polyoxazolidines produced in Examples 3 and 4).

The compositions of the single formulations are shown in Table 3, and also those diluted with xylene in the quantities indicated in the same Table.

under normal conditions, gave the results shown in Table 4.

The sheets, after being subjected to dynamomechanical characterization, were immersed in deionized water and submitted to hydrolyis in an oven at +65° C.

After two months of aging the polymeric films were removed from the acqueous bath and after drying and reconditioning, were subjected to dynamo-mechanical analysis. Whereas all the films based on oxazolidines having a carbonate structure are transparent, the films based on polyester are irreversibly opaque even after a short period of immersion in water, the dynamo-mechanical tests of Table 5 confirm the superiority of the polyoxazolidines having a polycarbonate structure compared to those having a polyester structure, in spite of initial more favourable result obtained by the latter

TABLE 4

| Test No | Thickness of sheet (mm) | Tens. Y (1) (N/mm$^2$) | U.T.S. (N/mm$^2$) | 5% Secant modulus (2) (N/mm$^2$) | 10% Secant modulus (3) (N/mm$^2$) | Elongation to brake (%) |
|---|---|---|---|---|---|---|
| 1 | 0.21 | 16.8 | 11. | 55.1 | 39.6 | 127 |
| 2 | 0.13 | 12.6 | 9.9 | — | 20.5 | 132 |
| 3 | 0.15 | 7.6 | 4.2 | 117 | 8.9 | 127 |
| | | | COMPARISON | | | |
| 4 | 0.09 | 35.2 | 24.114 | | 352.7 | 43.7 |

(1) Tens. Y . . . tensile strength corresponding to an ASTM yielding
(2) modulus at 5% elongation
(3) modulus at 10% elongation

TABLE 5

| Test No | Thickness of sheet (mm) | Tens. Y (N/mm$^2$) | U.T.S. (N/mm$^2$) | 5% Secant modulus (N/mm$^2$) | 10% Secant modulus (N/mm$^2$) | Elongation to brake (%) |
|---|---|---|---|---|---|---|
| 1 | 0.17 | 62 | 50.5 | 601 | 458 | 25 |
| 2 | 0.14 | 48 | 32 | 530 | 454 | 24 |
| 3 | 0.13 | 71 | 45.4 | 990 | 650 | 11.3 |
| | | | COMPARISON | | | |
| 4 | 0.12 | | fragile - completely opaque | | | |

TABLE 3

Applications of oxazolidine of examples 1-5 to paints

| TEST No | POLYOXAZOLIDINE EX. No | g | MEQ | DESMODUR N MEQ NCO | XYLENE ml |
|---|---|---|---|---|---|
| 1 | 1 | 9.03 | 105 | 119 | 150 |
| 2 | 1 | 7.7 | 59.5 | 85.7 | 150 |
| 3 | 3 | 9.93 | 115.9 | 92.7 | 180 |
| | | | COMPARISON | | |
| 4 | (*)9 | 9.63 | 86.7 | 80.7 | 150 |

(*)The polyoxazolidine used as a comparison is a polyoxazolidine containing polyester groups rather than polycarbonate groups and was prepared as described in Example 8.

The polyoxazolidines formulated as in Table 3 were in the form of sheets having a thickness of 0.1-0.2 mm for the evaporation of the xylene solvent, and the sheets, when examined after a week of cross-linking

EXAMPLE 8

A comparison of the oxazolidines of the previous examples was carried out using the following oxazolidine containing polyester groups:

Dimethylterephthalate (g 194.19, 1 mole), hydroxyethyl oxazolidine (g 349.8, moles 2.2) and sodium methylate (ml. 2.5 of a 30% solution by weight in methanol) were charged into the same reactor as Example 1.

The temperature was brought to 105° C.–110° C. and the vacuum in the reactor reduced to 0.5 mm.Hg within a period of an hour. The reaction was continued for a further 6 hours keeping the vacuum and temperature values constant and recovering a total of 64 g (100% of the theoretical value) of methanol and 18.6 g (58.5% of the theoretical value) of hydroxyethyl oxazolidine.

The product was cooled, the catalyst eliminated by adding p-toluenesulphonic acid and the product was then treated with CaO (10 g) heated ( 105° C.) and filtrated at that temperature. The yield was 449 g (100%).

Elemental analysis: C=64.08, H=8.16, N=6.22 (a structure with formula $C_{24}H_{32}O_6N_2$ requires MW 444, C=64.86, H=7.21, N=6.31) the viscosity: 1100 cps at +25° C. The NMR spectrum was in accordance with the proposed structure. The product crystallizes at r.t.

I claim:

1. Polyoxazolidines corresponding to the general formula (I):

where, n is a number between 1 and 10, R is a n-valent radioal selected from:
an N-ethyl-oxazolidinic radical a trivalent triethylisocyanurate radical, an n-valent alkylenic radical with a linear or branched chain, containing from 2 to 12 carbon atoms or a cycloalkylenic radical containing from 5 to 12 carbon atoms, the alkyl residue of a polyetheneglycol —($CH_2$—$CH_2$—O )$_m$—$CH_2$—$CH_2$— m being a number between 1 and 10, the para-dimethylenecyclohexane radical, or R is an n-valent radical having the general formula, where $R_3$ is the linear, cyclic or aryl hydrocarbon residue of a glycol containing up to 12 carbon atoms, whereas $R_4$ has the same meaning as R excluding R=N—ethyl-oxazoline radical;

$R_1$ and $R_2$ either the same or different, represent the hydrogen atom, an alkyl radical, having a linear or branched chain, containing from 1 to 6 carbon atoms, a cycloalkyl radical or an aryl radical or, $R_1$ and $R_2$ together with the carbon atom between them, represent a saturated cycloalkyl ring with 5, 6, or 7 carbon atoms.

2. Polyoxazolidines in accordance with claim 1, wherein R represents a linear or branched bi-, tri-, tetra-valent alkyenic radical containing from 2 to 6 carbon atoms or a cycloalkylenic radical;

$R_1$ and $R_2$ represent independently an alkyl radical, with a linear or branched chain, containing from 1 to 4 carbon atoms, or either $R_1$ or $R_2$ represents the hydrogen atom and the other represents an alkyl radical with a linear or branched chain, containing from 1 to 4 carbon atoms.

3. Process for the preparation of polyoxazolidines in accordance with claim 1 and or claim 2 wherein:
an aldehyde or a ketone (II):

is reacted with dihydroxyethylamine (III):

to give hydroxyethyloxazolidine (IV):
said hydroxyethyloxazolidine (IV) is reacted with a carbonate (V) and an alcohol (VI), R(—OH)$_n$   VI to give the polyoxazolidine (I);

R, $R_1$, $R_2$ and n having the meaning specified in claims 1 and 2 whereas, $R_5$ and $R_6$ represent a saturated or unsaturated hydrocarbon radical containing from 1 to 4 carbon atoms or an aryl radical or $R_5$ and $R_6$, together with the two adjacent oxygen atoms and the carbon atom between them form a cyclic carbonate with 5 or 6 atoms of the type where m is a number between 2 and 3.

* * * * *

UNITED STATES PATENT AND TRADEMARK OFFICE
CERTIFICATE OF CORRECTION

PATENT NO. : 5,219,979
DATED : June 15, 1993
INVENTOR(S) : Alberto Greco

It is certified that error appears in the above-indentified patent and that said Letters Patent is hereby corrected as shown below:

Column 4, Line 39, "$CH_3$" should read --"$CH_2$--

Column 14, Line 28, "by the latter" should read --by the latter.--

Column 15, Line 34, "a n-valent radioal" should read --a n-valent radical--

Column 16, Line 27, "claim 1 and or claim 2" should read --claim 1 or claim 2--

Signed and Sealed this

Eighteenth Day of October, 1994

Attest:

BRUCE LEHMAN

Attesting Officer          Commissioner of Patents and Trademarks